(12) United States Patent
Yamamoto et al.

(10) Patent No.: US 8,388,376 B2
(45) Date of Patent: Mar. 5, 2013

(54) ELECTRONIC ENDOSCOPE

(75) Inventors: Goki Yamamoto, Saitama (JP); Kazuaki Takahashi, Saitama (JP); Takashi Yashiro, Saitama (JP); Ryou Kitano, Saitama (JP); Kazushige Yamamoto, Saitama (JP)

(73) Assignee: Fujifilm Corporation, Tokyo (JP)

( * ) Notice: Subject to any disclaimer, the term of this patent is extended or adjusted under 35 U.S.C. 154(b) by 815 days.

(21) Appl. No.: 12/458,067

(22) Filed: Jun. 30, 2009

(65) Prior Publication Data
US 2009/0306475 A1  Dec. 10, 2009

(30) Foreign Application Priority Data
Jul. 1, 2008  (JP) ................................. 2008-172384

(51) Int. Cl.
*H01R 9/05* (2006.01)
(52) U.S. Cl. ......... 439/581; 600/101; 600/109; 600/139
(58) Field of Classification Search .................. None
See application file for complete search history.

(56) References Cited

U.S. PATENT DOCUMENTS

| | | | |
|---|---|---|---|
| 5,710,393 A | | 1/1998 | Smith et al. |
| 5,879,285 A | * | 3/1999 | Ishii ............................. 600/110 |
| 6,336,827 B1 | * | 1/2002 | Akama et al. ............ 439/607.46 |
| 7,269,896 B2 | * | 9/2007 | Edwardsen et al. ............. 29/828 |
| 7,345,312 B2 | * | 3/2008 | Kazakevich ..................... 257/81 |
| 2006/0292933 A1 | * | 12/2006 | van Meijl ..................... 439/610 |

FOREIGN PATENT DOCUMENTS

| JP | 09-098944 A | 4/1997 |
|---|---|---|
| JP | 2001-95758 | 4/2001 |

OTHER PUBLICATIONS

Kazuaki, Takahashi; Machine translation of JP 2001-095758; Apr. 10, 2001.*
Extended European Search Report dated Oct. 1, 2009.
Japanese Office Action dated Oct. 25, 2012 with English translation thereof.

* cited by examiner

*Primary Examiner* — Matthew J Kasztejna
*Assistant Examiner* — Alexandra Newton
(74) *Attorney, Agent, or Firm* — McGinn IP Law Group, PLLC

(57) ABSTRACT

An electronic endoscope has an insert section to be introduced into a human body cavity. A distal portion of the insert section contains a CCD and a printed circuit board to which the CCD is bonded. In the insert section, a cable bundle being a bundle of coaxial cables extends. Each coaxial cable consists of a signal line, insulation surrounding the signal line, a braided wire surrounding the insulation, and an insulating jacket. The cylindrical braided wire is stranded into a single line, and is soldered as a ground line to a ground terminal of the printed circuit board. The signal line is pulled out of the coaxial cable with a length longer than the ground line. The signal line is soldered to an input/output terminal of the printed circuit board with a larger sag than the ground line.

10 Claims, 9 Drawing Sheets

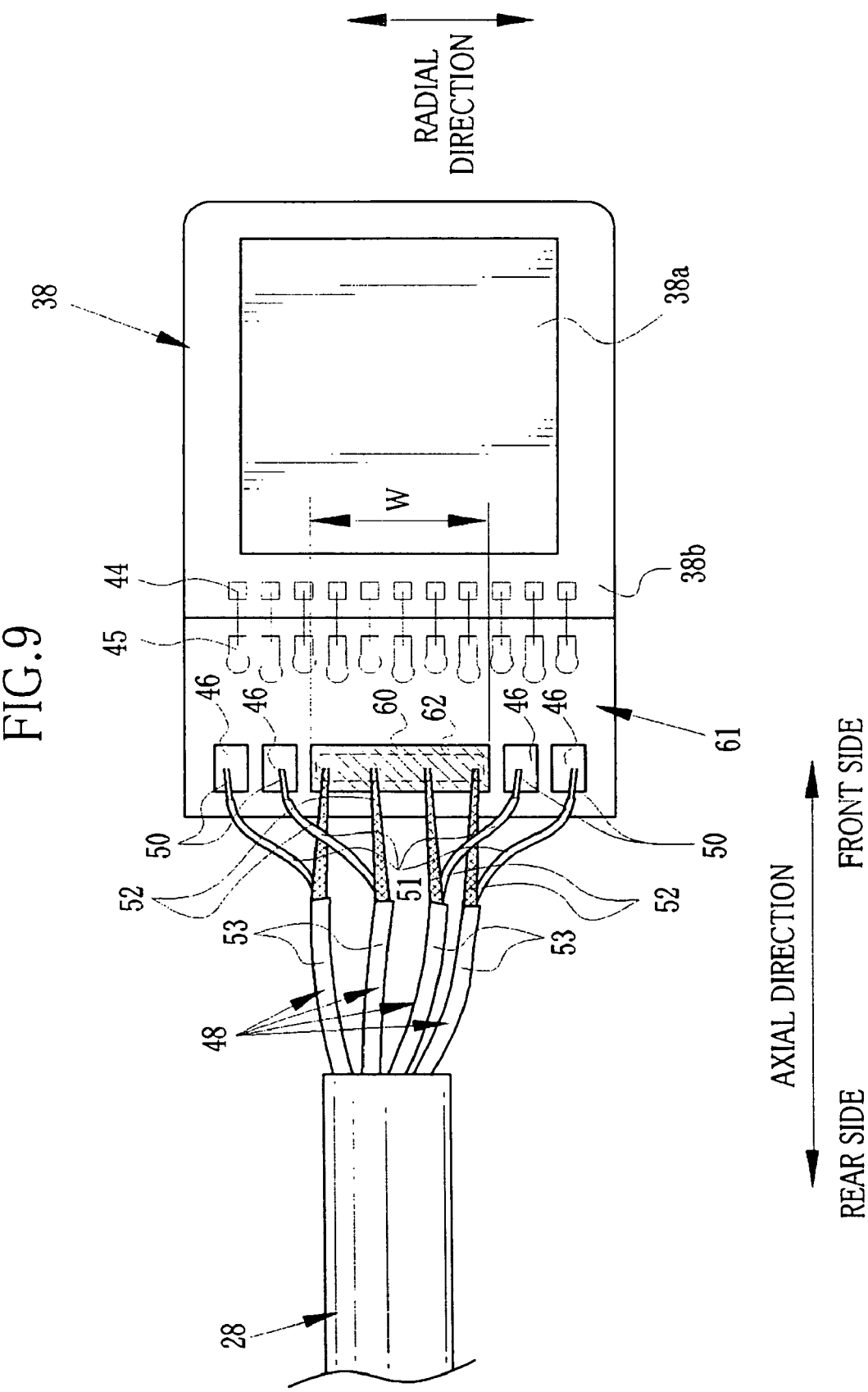

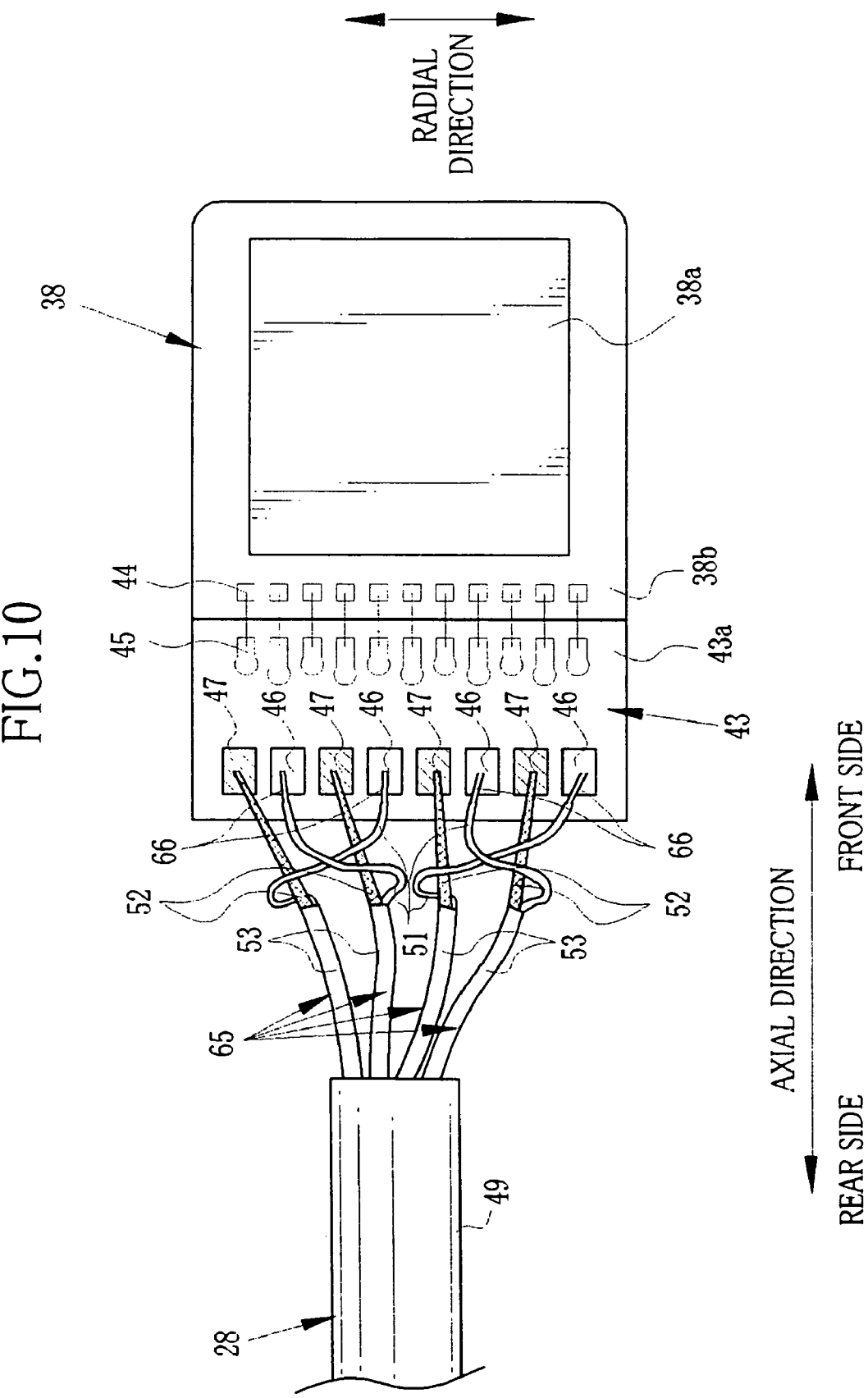

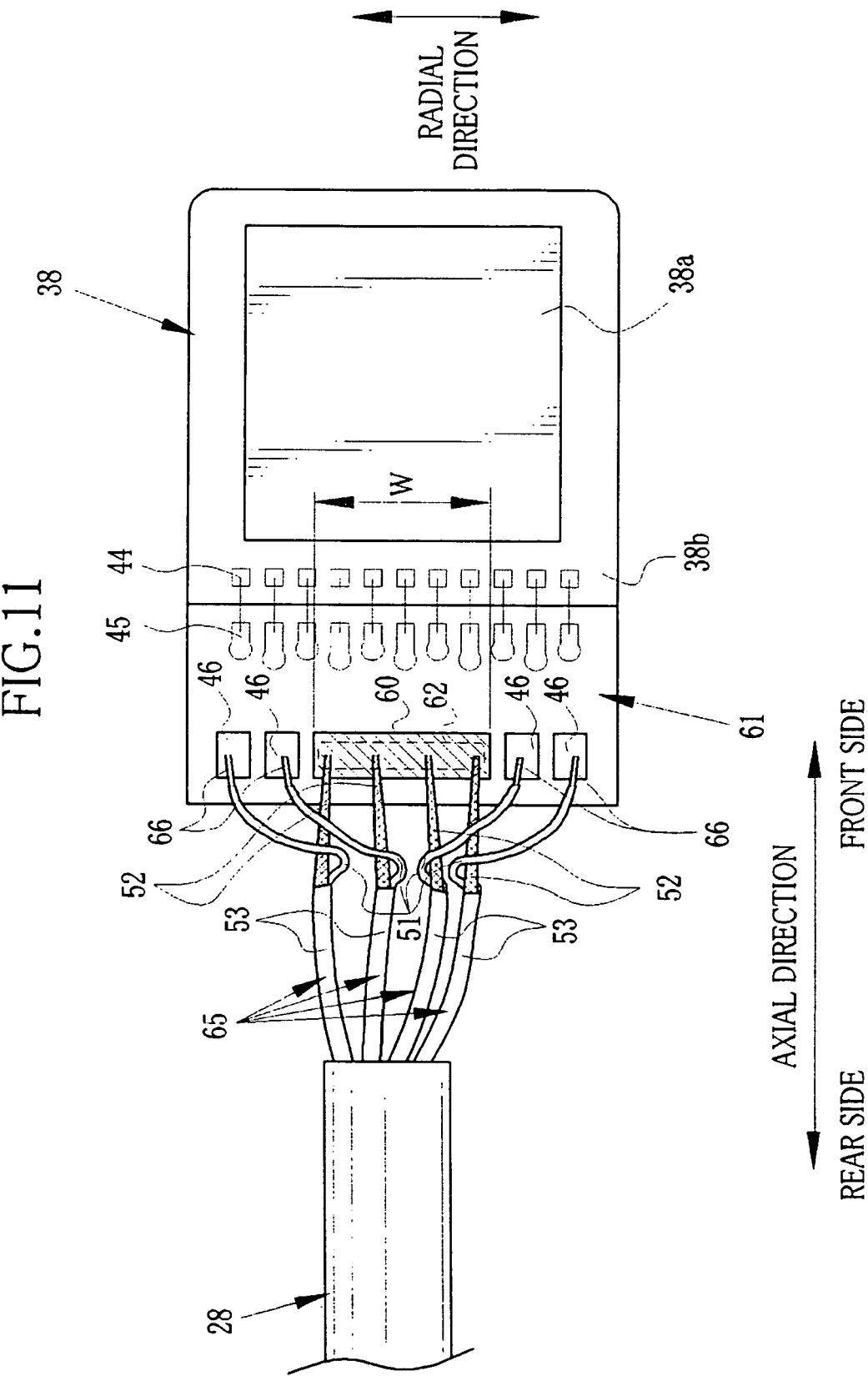

ELECTRONIC ENDOSCOPE

BACKGROUND OF THE INVENTION

1. Field of the Invention

The present invention relates to an electronic endoscope, and especially relates to the electronic endoscope having a connection structure between a coaxial cable and a solid-state image sensor.

2. Description Related to the Prior Art

An electronic endoscope has an insert section to be introduced into a human body cavity and an operation section for operating the insert section. The insert section is constituted of a distal portion, a bending portion, and a flexible portion arranged in this order from a distal end thereof. The distal portion is provided with an image capturing window, lighting windows, a medical instrument outlet, an airing/watering nozzle, and the like. Turning an angle knob on the operation section flexibly bends the bending portion from side to side and up and down to direct the distal portion in a desired direction inside the human body cavity.

The distal portion contains a solid-state image sensor that captures images of an internal body site through the image capturing window. To the solid-state image sensor, a printed circuit board is integrally attached. Signal cables connected to the printed circuit board extend through the insert section to the operation section. The insert section further contains angle wires for bending the bending section, a light guide for leading illumination light from a light source device to the lighting windows, and the like. An ultrasonic endoscope additionally has ultrasonic transducers provided at its distal portion and signal cables connected to the ultrasonic transducers.

As the signal cables connected to the printed circuit board, a cable bundle that consists of a plurality of bound coaxial cables is used. The coaxial cable consists of a center conductor positioned at the center thereof, insulation surrounding the center conductor, a braided wire surrounding the insulation, and an insulating jacket surrounding the braided wire. As described in Japanese Patent Laid-Open Publication No. 2001-95758, the center conductor is used as a signal line for transmitting an electrical signal between the solid-state image sensor and a processor device, and is joined to an input/output terminal of the printed circuit board by welding or the like. The braided wire is used as a ground line, and is joined to a ground terminal of the printed circuit board.

When the bending portion is bent into various directions in the human body cavity, the contents of the insert section shift in radial and axial directions of the insert section according to the bending. Thus, deformation stress applied to the cable bundle causes a break of a joint between the terminal of the printed circuit board and the coaxial cable.

The break of the joint occurs frequently in the center conductor used as the signal line. Since the braided wire in a net form is pulled out at an end of the insulating jacket of the coaxial cable, and is stranded into a single thick wire to be used as the ground line before being joined to the ground terminal, the braided wire has high strength and a firm solder joint. Since the center conductor, on the other hand, is just a single wire, the center conductor is inferior in strength to the braided wire and makes a weak solder joint. Japanese Patent Laid-Open Publication No. 2001-95758 neither describes a break of a joint nor takes measures thereto.

SUMMARY OF THE INVENTION

An object of the present invention is to provide an electronic endoscope that prevents a break of a joint between an input/output terminal of a printed circuit board and a coaxial cable.

An electronic endoscope according to the present invention includes a printed circuit board to which a solid-state image sensor is bonded and a plurality of coaxial cable extending in an insert section. The printed circuit board has a plurality of input/output terminals, and a plurality of ground terminals or a ground land. Each coaxial cable has a signal line joined to one of the input/output terminals and a ground line joined to one of the ground terminals or the ground land. The signal line is exposed from the coaxial cable with a length longer than the ground line exposed from the coaxial cable, and is joined to the input/output terminal with a larger sag than the ground line.

The signal line exists at the center of the coaxial cable with being surrounded by insulation. The ground line is a braid surrounding the insulation, and is stranded into a single line in the vicinity of the printed circuit board. It is preferable that the signal line be exposed from the axial cable 0.5 mm or more longer than the ground line. It is also preferable that the plural signal lines exposed from the coaxial cable cross with each other, and be then joined to the input/output terminals.

The input/output terminals and the ground terminals are alternately arranged in a direction orthogonal to an axis of the coaxial cable. The input/output terminals and the ground land may be arranged in a direction orthogonal to the axis of the coaxial cable. The ground land is positioned approximately in the middle of the arrangement, and the input/output terminals are arranged on both sides of the ground land.

The signal line of the coaxial cable may be pulled out on the opposite side of the input/output terminal to be joined relative to the ground line of the same coaxial cable. The signal line is joined to the input/output terminal over the ground line. It is preferable that a part of the signal line that is pulled out of the coaxial cable is bent in the shape of the letter "U".

According to the present invention, the signal line is pulled out of the coaxial cable longer than the ground line. Each signal line is joined to the corresponding input/output terminal with a larger sag than the ground line. Accordingly, since the ground line carries tension applied to the coaxial cable, it is possible to prevent the separation of the signal line from a solder joint and the like.

BRIEF DESCRIPTION OF THE DRAWINGS

For more complete understanding of the present invention, and the advantage thereof, reference is now made to the following descriptions taken in conjunction with the accompanying drawings, in which:

FIG. 9 is a plan view showing structure of the periphery of the CCD and the printed circuit board according to a second embodiment;

FIG. 10 is a plan view showing structure of the periphery of the CCD and the printed circuit board according to a third embodiment; and FIG. 11 is a plan view showing structure of the periphery of the CCD and the printed circuit board according to a fourth embodiment.

DESCRIPTION OF THE PREFERRED EMBODIMENTS

Figure 1:
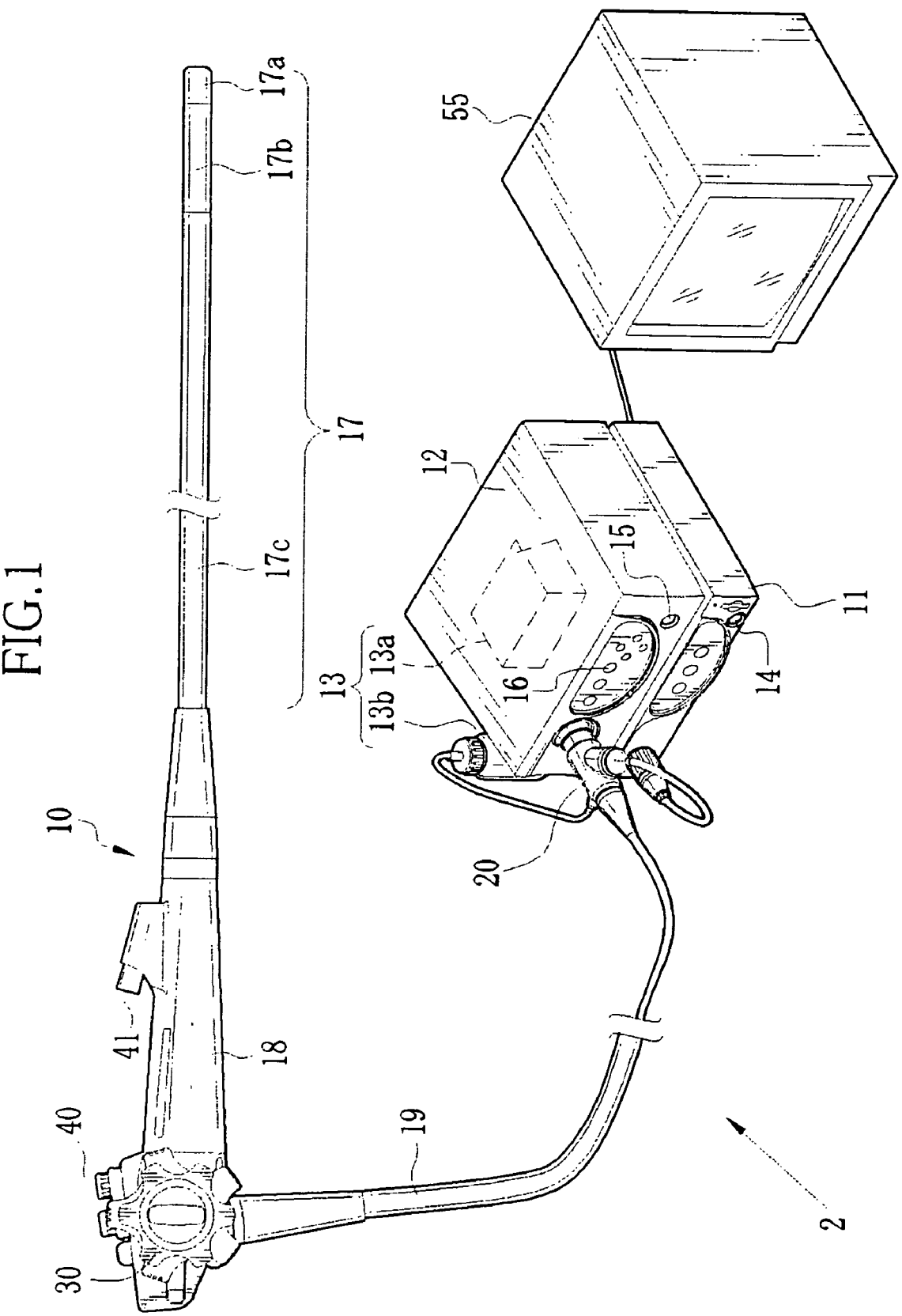
FIG. 1 is an overall view of an endoscope system.

As shown in FIG. 1, an endoscope system 2 is constituted of an electronic endoscope 10, a processor device 11, a light source device 12, and an airing/watering device 13. The airing/watering device 13 includes a commonly-known airing unit 13a for feeding air and a wash water tank 13b as a reservoir. The airing unit 13a is contained in the light source device 12, and the wash water tank 13b is provided outside the light source device 12. A power switch 14 is provided on a front face of the processor device 11 to turn the processor device 11 on and off. A front face of the light source device 12 is provided with a power switch 15 for turning the light source device 12 on and off and a light switch 16 for turning a light source (not illustrated) on and off.

The electronic endoscope 10 is constituted of an insert section 17 to be inserted into a human body cavity, an operation section 18 coupled to a base end of the insert section 17, and a universal cord 19 connected to the processor device 11 and the light source device 12. To an end of the universal cord 19, a multi-connector 20 is attached. The multi-connector 20 is connected to the processor device 11 and the light source device 12. The processor device 11 applies image processing to an image signal, which is inputted from a solid-state image sensor e.g. a CCD 38 (refer to FIG. 4) through the universal cord 19 and the connector 20, to convert the image signal into a video signal. The processor device 11 sends a drive control signal to control the actuation of the CCD 38. The video signal produced by the processor device 11 is displayed as endoscope images on a monitor 55 connected to the processor device 11 with a wire. The processor device 11 is electrically connected to the light source device 12, and controls the operation of the entire endoscope system 2.

The slender insert section 17 has a distal portion 17a, a bending portion 17b, and a flexible portion 17c arranged in this order from its distal end. The rigid distal portion 17a contains the CCD 38 (refer to FIG. 4). Operating the operation section 18 forcefully bends the bending portion 17b to aim the distal portion 17a at a desired direction. The flexible portion 17c naturally curves according to the shape of organs in the human body cavity.

Figure 2:
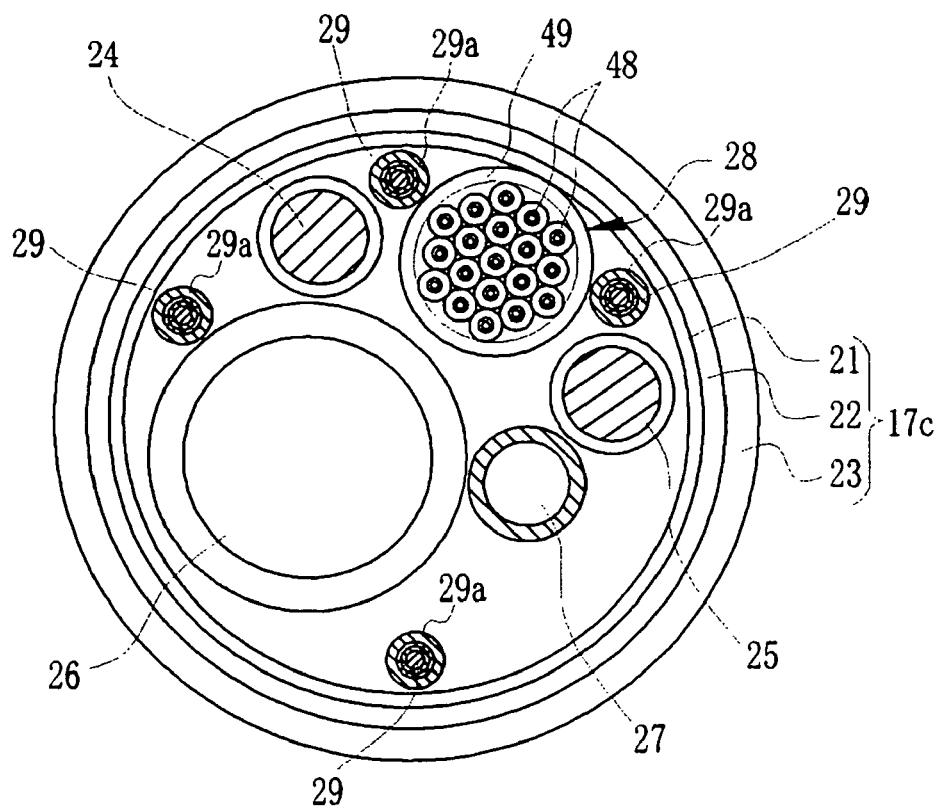
FIG. 2 is a cross sectional view of a flexible portion.

As shown in FIG. 2, the flexible portion 17c consists of three layers, that is, a helical tube 21 called flex, a metal net 22 called braid, and an outer jacket 23. The helical tube 21 is made of a helically wound metal strip. The pipe-shaped net 22 coats the helical tube 21 to prevent the metal strip from loosening and as a base for the outer jacket 23. The outer jacket 23 is a resin layer extruded on the net 22. The flexible portion 17c contains a plurality of components such as light guides 24 and 25 for leading illumination light, a medical instrument channel 26, an airing/watering channel 27, a cable bundle 28, and angle wires 29.

The angle wires 29 are fixed on the distal portion 17a. The angle wire 29, which extends through a tightly wound coil pipe 29a, is pushed and pulled inside the coil pipe 29a in conjunction with the operation of an angle knob 30 (refer to FIG. 1) provided on the operation section 18. The bending portion 17b, consisting of a number of articulated segments, flexibly bends from side to side and up and down in response to pushing and pulling the angle wires 29. Accordingly, the distal portion 17a is aimed at a desired direction inside the human body cavity, and the CCD 38 can capture images of a target body site inside the human body cavity.

Figure 3:
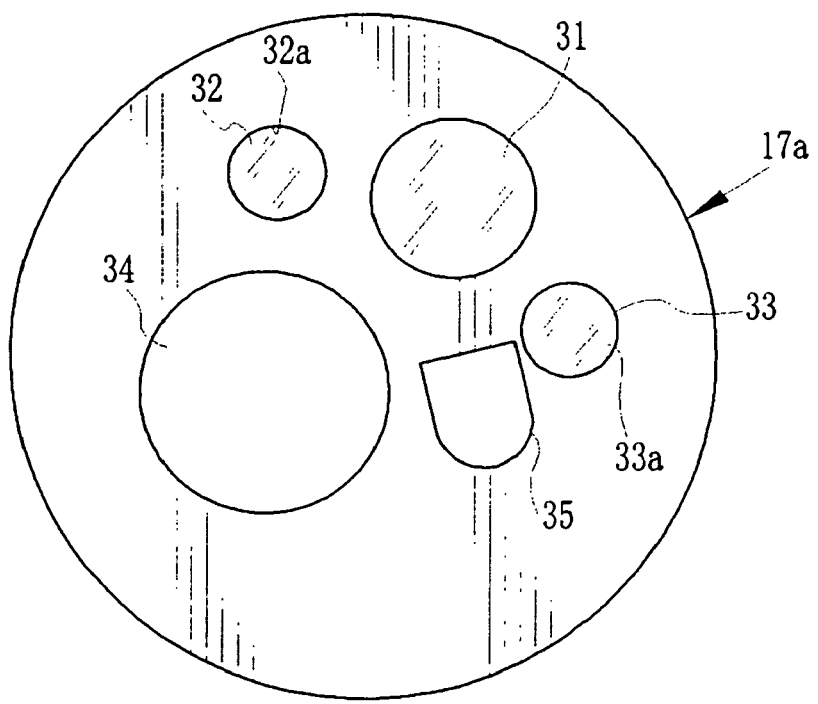
FIG. 3 is a front view of a distal portion.
Figure 4:
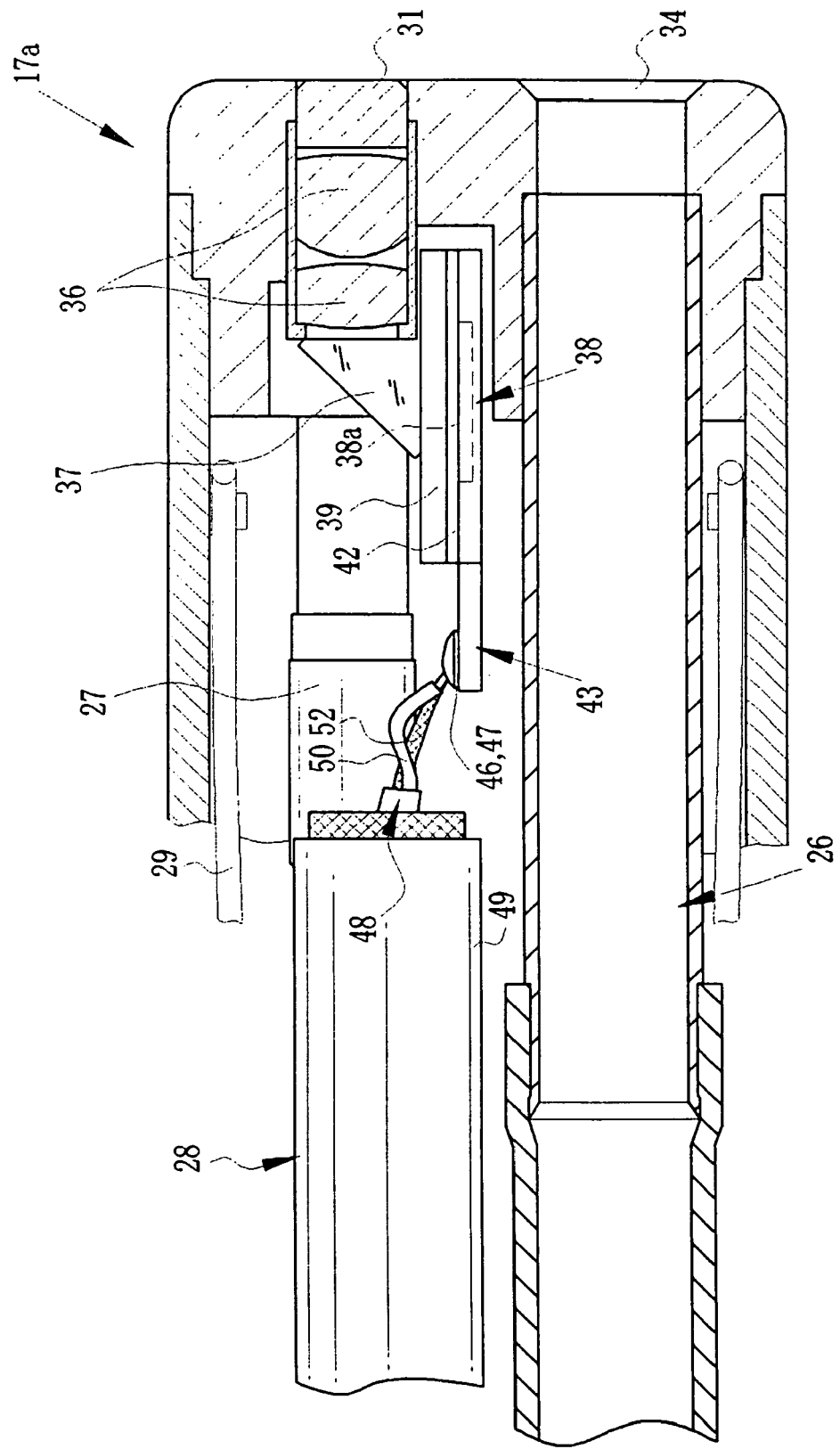
FIG. 4 is a longitudinal sectional view of the distal portion.

Referring to FIGS. 3 and 4, a front face of the distal portion 17a is provided with an image capturing window 31, lighting windows 32 and 33, a medical instrument outlet 34, and an airing/watering nozzle 35. Behind the image capturing window 31, an objective optical system 36 is disposed to capture image light in the human body cavity. The image light of the target body site, which has passed through the objective optical system 36, is totally reflected by a prism 37, and forms an image on an imaging surface 38a of the CCD 38. The prism 37 is fixed on a cover glass 39.

Lighting lenses 32a and 33a are fitted into the lighting windows 32 and 33, respectively. The lighting lens 32a faces to a light emitting end of the light guide 24, and the lighting lens 33a faces to a light emitting end of the light guide 25. Each light guide 24 or 25 consists of, for example, a bundle of many glass optical fibers. When the connector 20 is connected to the light source device 12, the light guides 25 and 26, which extend through the insert section 17, the operation section 18, the universal cord 19, and the connector 20, lead the illumination light from the light source device 12 to the lighting windows 32 and 33, and apply the illumination light to the target body site inside the body cavity.

The airing/watering nozzle 35 is coupled to the airing/watering channel 27. Operating an airing/watering button 40 (refer to FIG. 1) provided on the operation section 18 sprays wash water from the airing/watering device 13 on the image capturing window 31 for cleaning. After the cleaning, blowing air on the image capturing window 31 removes water droplets. The medical instrument outlet 34 is coupled to the medical instrument channel 26. A medical instrument having a pair of forceps, a syringe, a knife, or the like at its tip is inserted from a medical instrument insertion port 41 (refer to FIG. 1) into the medical instrument channel 26, so that the tip of the instrument projects from the medical instrument outlet 34 in the human body cavity to perform surgical procedures on the target body site.

The CCD 38 is, for example, an interline transfer CCD. The CCD 38 is in a state of bare chip that has the imaging surface 38a on its top. A rectangular frame-shaped spacer 42 is attached around the imaging surface 38a of the CCD 38, and the rectangular cover glass 39 is attached on the spacer 42.

Figure 5:
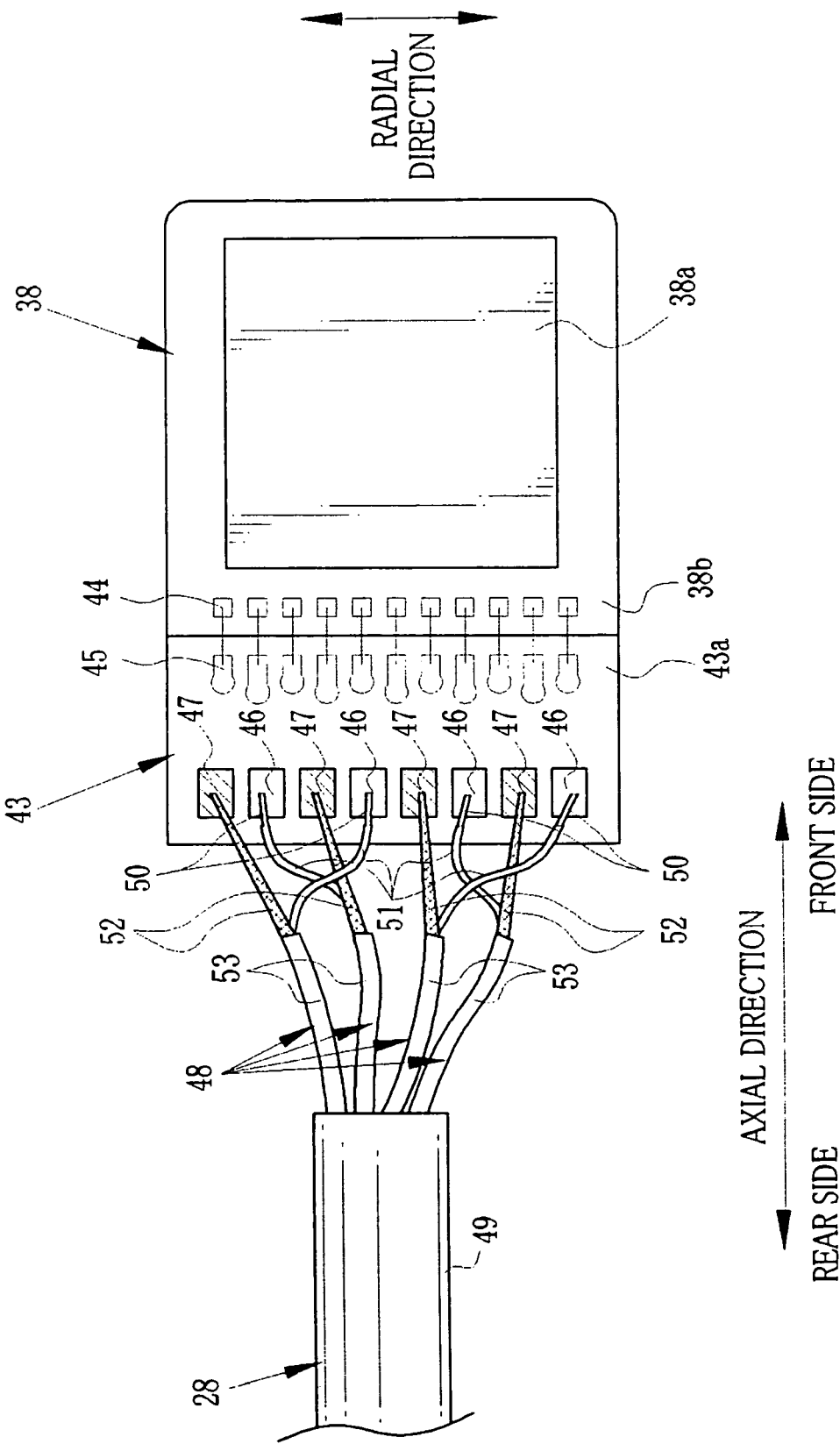
FIG. 5 is a plan view showing structure of the periphery of a CCD and a printed circuit board according to a first embodiment.

As shown in a double-headed arrow of FIG. 5, an axial direction refers to a longitudinal direction of the insert section 17. A front side refers to a side of the image capturing window 31 of the distal portion 17a, and a rear side refers to the opposite. A radial direction refers to a direction orthogonal to the axial direction and horizontal to a chip of the CCD 38. To a rear end face of the CCD 38, a printed circuit board (PCB) 43 that has approximately the same thickness as the CCD 38 is attached. Bonding pads 44 are densely laid out in a rear margin 38b of the CCD 38. On the other hand, PCB bonding pads 45 are densely laid out in a front margin 43a of the printed circuit board 43, which is opposed to the rear margin 38b. The bonding pad 44 is electrically bonded to the PCB bonding pad 45 with a bonding wire or the like. Otherwise, the printed circuit board 43 may be attached on a rear face of the CCD 38.

In the printed circuit board 43, an equal number of input/output terminals 46 and ground terminals 47 are provided at the rear of the PCB bonding pads 45. The input/output terminals 46 and the ground terminals 47 are alternately arranged. The ground terminals 47 are shaded in FIGS. 5, 8, and 9 for the purpose of clearly distinguishing between the input/output terminals 46 and the ground terminals 47. The input/output terminals 46 and the ground terminals 47 are aligned in the radial direction.

The cable bundle 28 consists of a bundle of coaxial cables 48 and a jacket 49 surrounding the bundle (refer to FIG. 2). At an end of the cable bundle 28 on the side of the printed circuit board 43, the jacket 49 is stripped off to expose the coaxial cables 48.

Figure 6:
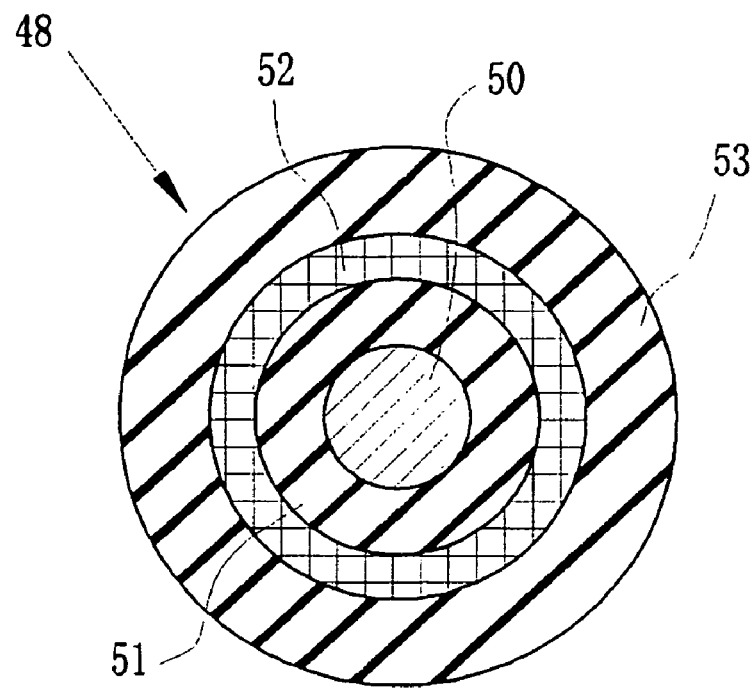
FIG. 6 is a cross sectional view of a coaxial cable.

In FIG. 6, each coaxial cable 48 consists of a signal line (center conductor) 50, insulation (insulating tube) 51 surrounding the signal line 50, a ground line (braided wire) 52 surrounding the signal line 50 via the insulation 51, and an insulating jacket 53 further surrounding the ground line 52. The insulating jacket 53 and the insulation 51 are stripped off in the vicinity of the printed circuit board 43 to expose and/or pull out the signal line 50 and the ground line 52.

Returning to FIG. 5, the signal line 50 is soldered to the input/output terminal 46 of the printed circuit board 43 with a larger sag than the ground line 52. The ground line 52 includes a plurality of braided thin wires. The thin wires exposed in the vicinity of the printed circuit board 43 are stranded into a single line. Then, the ground line 52 is soldered to ground terminal 47 on a one-by-one basis.

Figure 7:
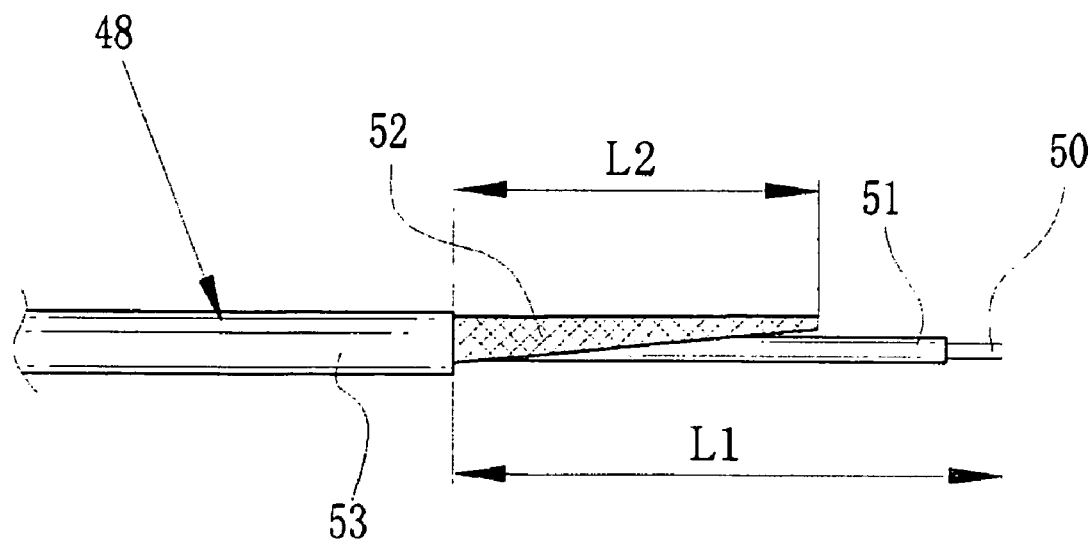
FIG. 7 is an explanatory view showing the lengths of a signal line and a ground line.

As shown in FIG. 7, the length (signal line exposure length) L1 of the signal line 50 exposed to the outside from the insulating jacket 53 of the coaxial cable 48 is longer than the length (ground line exposure length) L2 of the ground line 52 (L1>L2). It is preferable that the difference between the signal line exposure length L1 and the ground line exposure length L2 be 0.5 mm or more. When the signal line exposure length L1 is longer than the ground line exposure length L2, and the signal line 50 is soldered to the input/output terminal 46 with the sag, the ground line 52 of the short exposure length carries substantially all the load that is applied to the coaxial cable 48 by pulling the cable bundle 28 backward. Since there is substantially no tensile load on the signal line 50, it is possible to prevent a break of the signal line 50 and separation of the signal line 50 from a solder joint.

On the other hand, the ground line 52, which consists of a bundle of braided thin wires, is superior in strength and hard to break even with the tensile load applied by the coaxial cable 48. The ground line 52 is a net of plural wires and thicker in size. Accordingly, the ground line 52 has a large soldering area, and hence is of high connection strength to the ground terminal 47 and hard to separate therefrom.

The signal line 50 pulled out of the coaxial cable 48 crosses with another signal line 50 of the adjoining coaxial cable 48, and is not joined to the nearest input/output terminal 46 but to the farther input/output terminal 46. This is because of reducing the curvature of the signal line 50.

Figure 8A:
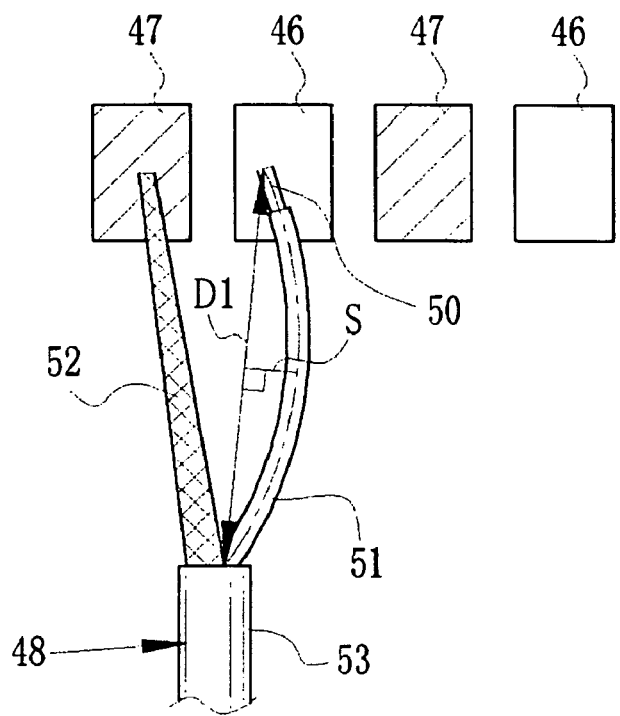
FIG. 8A is an explanatory view showing a sag of the signal line when the signal line is bonded to the nearest input/output terminal.
Figure 8B:
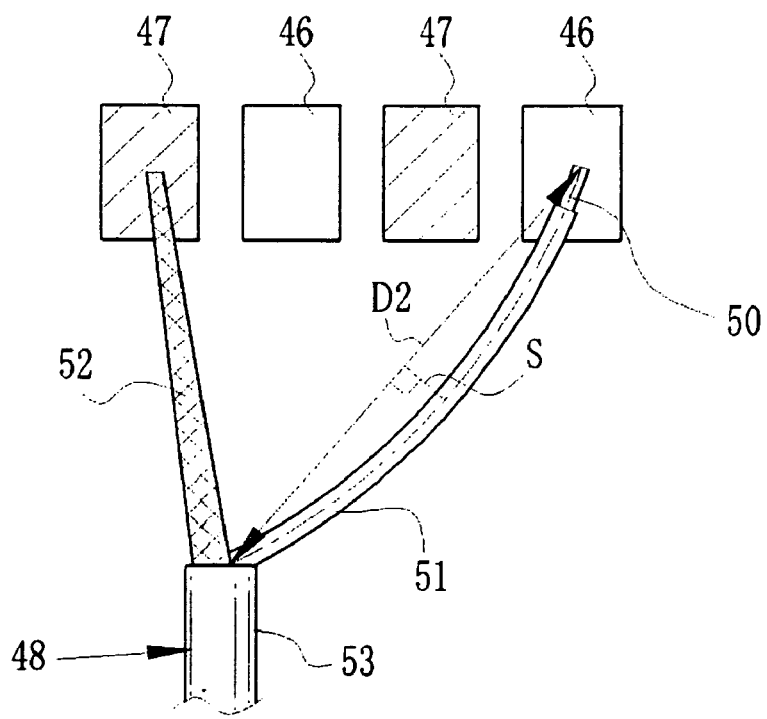
FIG. 8B is an explanatory view showing a sag of the signal line when the signal line is bonded to a farther input/output terminal.

More specifically, when the signal line 50 has a sag "S", connecting the signal line 50 to the farther input/output terminal 46 as shown in FIG. 8B results in reduction in the curvature of the signal line 50, as compared with the case of connecting the signal line 50 to the nearest input/output terminal 46 as shown in FIG. 8A. Referring to FIGS. 8A and 8B, "chord" refers to a straight line between a base end of the signal line 50 being a point where the signal line 50 is pulled out of the coaxial cable 48 and the other end being a point where the signal line 50 is joined to the input/output terminal 46. The length of chord of FIG. 8A is "D1", and that of FIG. 8B is "D2". "Arc" shown by a dash-dotted line refers to a path of the signal line 50 with the sag. At this time, the maximum length of the normal from arc to chord is referred to as the sag "S". When the sag "S" is constant, the curvature of arc reduces with increase in the length of chord. Since the chord "D2" of FIG. 8B is longer than the chord "D1" of FIG. 8A, the curvature of the signal line 50 is less in FIG. 8B.

When the curvature of the signal line 50 is too large, the so-called "kink", where the bent signal line 50 is plastically deformed and does not return to an original shape, tends to occur. Intersecting the signal lines 50 of the adjoining coaxial cables 48 with each other, and joining the signal cables 50 to the farther input/output terminals 46, respectively, make it possible to reduce the curvature of the signal lines 50 with the sag "S" and hence prevent the occurrence of kink.

Increasing the distance between the input/output terminal 46 and the ground terminal 47, that is, increasing a linear distance "D" reduces the curvature without intersecting the signal lines 50 of the adjoining coaxial cables 48 with each other, as a matter of course. Increase in the distance, however, results in upsizing the printed circuit board 43. According to the present invention, intersecting the signal lines 50 makes it possible to reduce the curvature of the signal line 50 without upsizing the printed circuit board 43.

In this embodiment, the signal line 50 intersects with another signal line 50 of the next coaxial cable 48, but may intersect with further another signal line 50 of the coaxial cable 48 after the next.

In using the endoscope system 2, after the connector 20 of the electronic endoscope 10 is inserted into the processor device 11 and the light source device 12, are turned on the power switch 14 of the processor device 11 and the power switch 15 and the light switch 16 of the light source device 12. Turning on the power switches 14 and 15 energizes the processor device 11 and the light source device 12. The processor device 11 feeds electric power to the electronic endoscope 10 and actuates the CCD 38.

The light source of the light source device 12 is turned on, and the CCD 38 is actuated to capture the images inside the human body cavity. A doctor operates the angle knob 30 to bend the bending portion 17b and change the angle of the distal portion 17a with respect to the flexible portion 17c, for the purpose of viewing the target body site from another direction. In response to bending the bending portion 17b in various directions, the signal lines 50 and the ground lines 52 of the coaxial cables 48 are pulled and twisted in the axial and radial directions. However, the signal lines 50 are joined to the printed circuit board 43 with the larger sag than the ground lines 52, as described above, so that a load due to the pull or the twist is mainly applied to the ground lines 52. Thus, it is possible to prevent a break of the signal line 50 and separation of the signal line 50 from the solder joint. The ground line 52 is stronger and has higher soldering strength than the signal line 50. Accordingly, the ground line 52 has higher resistance to breaking and separation from the solder joint even with the pull and the twist.

A second embodiment of the present invention will be hereinafter described. In the foregoing first embodiment, the ground lines 52 of the plural coaxial cables 48 are joined to the separate ground terminals 47 one by one, but the plural ground lines 52 may be joined to a single ground terminal (ground land) 60 as shown in FIG. 9. In a printed circuit board 61 shown in FIG. 9, the input/output terminals 46 and the ground land 60 are aligned in the radial direction, as with the foregoing printed circuit board 43. To the single ground land 60, the plural ground lines 52 are joined with appropriate intervals. The ground land 60 is positioned in the middle of the alignment, and the two input/output terminals 46 are disposed on both sides thereof. The width "W" of the ground land 60 is wider than that of the ground terminal 47 according to the first embodiment.

In the second embodiment, a plurality of ground lines 52 is soldered to the ground land 60 at a time. In this case, connection strength between a solder joint 62 (illustrated by a dotted line) and the plural ground lines 52 is increased, as compared with soldering the ground lines 52 to the ground terminals 47 one by one. Since the ground land 60 is disposed in the middle of a rear margin in the radial direction and the input/output terminals 46 are disposed on both sides thereof, each of the two signal lines 50 pulled out of the two coaxial cables 48 positioned in the middle of the cable bundle 28 intersects with the ground line 52 of the adjoining coaxial cable 48 and has a long linear distance (chord) "D". Accordingly, it is possible to reduce the curvature of the sagging signal line 50 and prevent the occurrence of kink.

The ground land 60 may not be positioned in the middle of the rear margin in the radial direction. Even in this case, joining the plural ground lines 52 to the single ground land 60 has the advantage of increasing the connection strength. Otherwise, a plurality of ground lands 60 may be provided. In FIG. 9, for example, the ground land 60 may be divided in two and two ground lines 52 may be joined to each of the divided ground land.

In a third embodiment shown in FIG. 10, further sagging signal lines 66 are joined to the input/output terminals 46. The signal line 66 is pulled out of a coaxial cable 65 from the opposite side of the input/output terminal 46 to be joined. The signal line 66 is bent in the shape of the letter "U", and is joined to the input/output terminal 46 over the ground line 52. The other respects of the coaxial cable 65 are the same as those of the coaxial cable 48 according to the foregoing embodiments. As described above, since the signal line 66 is folded over the ground line 52 and then joined to the input/output terminal 46, the signal line 66 has a larger sag than the signal line 50 of the first embodiment.

FIG. 11 shows a fourth embodiment having a large-sized single ground land 60. As with the third embodiment shown in FIG. 10, the signal line 66 is pulled out of the coaxial cable 65 from the opposite side of the input/output terminal 46 to be joined relative to the ground line 52 of the same coaxial cable 65, and is joined to the input/output terminal 46 over the ground line 52. Since the signal line 66 is folded over the ground line 52 and then joined to the input/output terminal 46, the signal line 66 has a larger sag than the signal line 50 of the second embodiment.

The present invention is applicable to an ultrasonic endoscope, which has ultrasonic transducers in its distal portion 17a, or the like, in addition to the electronic endoscope 10.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope comprising a flexible insert section for introducing into a human body cavity, said insert section comprising a solid-state image sensor at its tip for capturing an image of an internal body site, said electronic endoscope comprising:
   a printed circuit board to which said solid-state image sensor is bonded, said printed circuit board comprising a plurality of input/output terminals, and a plurality of ground terminals or a ground land; and
   a plurality of coaxial cables extending in said insert section, each of said coaxial cables comprising a signal line joined to one of said input/output terminals and a ground line joined to one of said ground terminals or ground land, said signal line being exposed from said coaxial cable and being joined to said input/output terminal with a larger sag than said ground line,
   wherein only the signal line of one of the coaxial cables crosses with the signal line and the ground line of another one of the coaxial cables.

2. The electronic endoscope as recited in claim 1, wherein said signal line exists at a center of said coaxial cable with being surrounded by insulation, and said ground line comprises a braid surrounding said insulation, and is stranded into a single line in a vicinity of said printed circuit board.

3. The electronic endoscope as recited in claim 1, wherein said signal line is exposed from said axial cable 0.5 mm or more longer than said ground line.

4. The electronic endoscope as recited in claim 1, wherein said signal lines exposed from said coaxial cables cross with each other, and then are joined to said input/output terminals.

5. The electronic endoscope as recited in claim 1, wherein said input/output terminals and said ground terminals are alternately arranged in a direction orthogonal to an axis of said coaxial cable.

6. The electronic endoscope as recited in claim 5, wherein said input/output terminals and said ground land are arranged in the direction orthogonal to said axis of said coaxial cable, said ground land is positioned approximately in a middle of said arrangement, and said input/output terminals are arranged on both sides of said ground land.

7. The electronic endoscope as recited in claim 1, wherein said signal line of said coaxial cable is pulled out on an opposite side of said input/output terminal to be joined relative to said ground line out of a same coaxial cable, and is joined to said input/output terminal over said ground line.

8. The electronic endoscope as recited in claim 1, wherein a part of said signal line that is pulled out of said coaxial cable is bent in a "U" letter shape.

9. The electronic endoscope as recited in claim 1, wherein the signal line of said one of the coaxial cables is connected to one of the input/output terminals that, in a radial direction of the printed circuit board, is located farther than another one of the input/output terminals, which is located adjacent to one of the ground terminal connected to the ground line of said one of the coaxial cable.

10. The electronic endoscope as recited in claim 1, wherein said sag is defined as a maximum length of a normal from an arc of a path of the signal line to a chord of the signal line, said chord being defined as a straight line between a base end of the signal line where the signal line is pulled out of said each of the coaxial cable and another end of the signal line where the signal line is joined to said input/output terminal.

* * * * *